US008053399B2

(12) United States Patent
Seidling et al.

(10) Patent No.: US 8,053,399 B2
(45) Date of Patent: Nov. 8, 2011

(54) FOAMABLE COMPOSITIONS

(75) Inventors: Jeffrey R. Seidling, Neenah, WI (US); Scott W. Wenzel, Neenah, WI (US); Corey Thomas Cunningham, Larsen, WI (US); Pierre Joseph, Hamilton, NJ (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 395 days.

(21) Appl. No.: 11/847,772

(22) Filed: Aug. 30, 2007

(65) Prior Publication Data

US 2009/0062176 A1 Mar. 5, 2009

(51) Int. Cl.
*A61K 7/06* (2006.01)
(52) U.S. Cl. ......................... 510/119; 424/401; 424/400
(58) Field of Classification Search .................. 510/119; 424/401, 400
See application file for complete search history.

(56) References Cited

U.S. PATENT DOCUMENTS 4,147,306 A * 4/1979 Bennett ......................... 239/327
6,053,364 A 4/2000 Van der Heijden
6,087,310 A * 7/2000 Henkel ......................... 510/138
6,287,580 B1 * 9/2001 Gott et al. ..................... 424/401
6,287,581 B1 * 9/2001 Krzysik et al. ................ 424/402
6,290,104 B1 9/2001 Bougamont
6,344,205 B1 * 2/2002 Grimm et al. ................. 424/401
6,423,329 B1 7/2002 Sine et al.
6,534,069 B1 * 3/2003 Asmus et al. ................. 424/401
6,536,629 B2 3/2003 van der Heijden
7,214,382 B2 * 5/2007 Shefer et al. .................. 424/401
2004/0253198 A1 12/2004 Shefer
2005/0048090 A1 * 3/2005 Rau .............................. 424/401
2005/0129626 A1 6/2005 Koivisto
2006/0182690 A1 * 8/2006 Veeger et al. ................... 424/45
2007/0053853 A1 * 3/2007 Hurley et al. ................... 424/59
2007/0065383 A1 3/2007 Fernandez de Castro
2007/0179207 A1 8/2007 Fernandez de Castro

OTHER PUBLICATIONS

Disclosure of U.S. Patent Application.
Office Action of May 12, 2008.

* cited by examiner

*Primary Examiner* — Milton I Cano
*Assistant Examiner* — Mohammad Asdjodi
(74) *Attorney, Agent, or Firm* — Dority & Manning, P.A.

(57) ABSTRACT

Foamable compositions are disclosed. The compositions contain one or more active ingredients combined with a foaming agent and optionally one or more surface tension adjusting agents. The foaming agent may comprise, for instance, a derivatized dimethicone. The surface tension adjusting agent, on the other hand, comprises a chemical species that either increases or decreases the surface tension of the composition within a desired range so that the composition is readily foamable. In this manner, active ingredients can be incorporated into the compositions that are typically hard to foam. Such ingredients include cleaning solvents and various skin care agents. Of particular advantage, foamable compositions can be formulated in accordance with the present disclosure that contain relatively small amounts of water such as less than about 20 percent by weight, such as less than about 10 percent by weight. In other embodiments, the composition can be completely anhydrous.

27 Claims, 1 Drawing Sheet

FOAMABLE COMPOSITIONS

BACKGROUND

Recently, consumer foamable cleansers have appeared on the market. Foamable cleansers are typically kept in a dispensing container that mixes the cleansing composition with air when dispensed immediately forming a foam or lather. These types of products have been used extensively in the medical field by doctors and other medical personnel. Compositions dispensed as foams have been regarded as desirable in part because of an association of foam with cleaning ability.

One problem that has been experienced in formulating foamable compositions, however, is the ability to incorporate certain useful chemicals into the compositions. For example, many useful chemicals are anhydrous and typically act as defoaming agents or foam depressants making their incorporation into foamable compositions somewhat problematic. For example, many cleaning solvents, such as solvents used to remove paint and/or grease, and many skin care agents, such as warming agents, reduce the surface tension of water and other liquids below that needed to maintain the integrity of the lamellae of a foam bubble. Such anhydrous ingredients also display surfactant molecules at the air/water interface disrupting the stability of any foam being formed and causing collapse. In addition, some of the above ingredients lose their effectiveness when combined with water, which has traditionally been used as a foam carrier in foamable compositions due to its polar nature.

In view of the above, a need currently exists for foamable compositions capable of containing difficult to foam ingredients, such as cleaning solvents and skin care agents. In addition, a need exists for a foamable composition that can produce a high quality foam while containing substantially no water.

SUMMARY

In general, the present disclosure is directed to foamable compositions containing various useful chemicals. More particularly, the present disclosure is directed to foamable compositions containing “hard to foam” ingredients, such as various anhydrous ingredients. Compositions of the present disclosure can include, for instance, a foam building base capable of incorporating various useful chemicals into a foamable composition such as cleaning solvents, skin care agents and the like. In one embodiment, for instance, a foamable composition can be formulated that contains substantially no water or is anhydrous. In other embodiments, however, water may be present in the composition in a manner such that the water does not interfere with the other components and allows the composition to foam when combined with a gas, such as air.

In one embodiment, for instance, the present disclosure is directed to a foamable composition comprising a skin care agent, such as a warming agent that causes the composition to increase in temperature when contacted with water. The warming agent may comprise, for instance, glycerin, a glycerin derivative, a glycol, or mixtures thereof. In order to cause the warming agent to foam, the composition can further contain a foaming agent and a surface tension adjusting agent. The foaming agent, for instance, may comprise a derivatized dimethicone. The surface tension adjusting agent may comprise any suitable agent that lowers the surface tension of the composition. For instance, in one embodiment, the surface tension adjusting agent may comprise a monofunctional alcohol, such as ethanol.

Of particular advantage, the above foamable composition can be formulated without containing any substantial amounts of water. For instance, in one embodiment, the composition can be anhydrous.

Various different derivatized dimethicone foaming agents may be used in the composition of the present disclosure. The derivatized dimethicone, for instance, may comprise a dimethicone copolyol, such as an ethoxylated dimethicone. In one embodiment, the derivatized dimethicone is linear, although pendant dimethicones may be used.

Particular examples of dimethicone copolyols that may be used include polyoxyethylene glycol dimethicone containing from about 5 to about 20 moles of polyoxyethylene glycol. The derivatized dimethicone may be, for instance, PEG-10 dimethicone, PEG-12 dimethicone, or mixtures thereof.

In one embodiment, the derivatized dimethicone may comprise a dimethicone copolyol ester. An example, for instance, of a dimethicone copolyol ester is dimethicone PEG-7 cocoate.

The derivatized dimethicone may be present in the composition in an amount sufficient to cause the composition to foam when combined with air. For instance, the derivatized dimethicone may be present in the composition in an amount from about 0.5 percent to about 30 percent by weight, such as from about 3 percent to about 26 percent by weight.

As described above, in this embodiment, the composition contains a warming agent which may be glycerin, a glycerin derivative, or a glycol. Glycerin derivatives that may be used as the warming agent include ethoxylated glycerin derivatives, such as methyl gluceth containing from about 5 moles to about 50 moles of ethoxylate. Methyl gluceth can be obtained from various commercial sources including the Lubrizol Corporation of Wickliffe, Ohio. Methyl gluceth may be produced from glucose obtained, for instance, from corn and methyl alcohol.

Glycols that may be used as warming agents include butylene glycol, propylene glycol, polyethylene glycol, ethoxydiglycol, hexylene glycol, and mixtures thereof.

The amount of warming agent present in the composition in conjunction with the surface tension adjusting agent can vary depending upon the particular application and the components present. The warming agent may be present in the composition, for instance, in an amount from at least about 15 percent to about 90 percent by weight, such as from about 20 percent to about 80 percent by weight, and, in one embodiment, from about 30 percent to about 70 percent by weight. The surface tension adjusting agent, on the other hand, is generally present in an amount sufficient to adjust the surface tension of the resulting composition so that the composition will foam when aerated. For instance, in one embodiment, the surface tension adjusting agent is present such that the warming agent and the surface tension adjusting agent present in the composition have a weight average surface tension based on 10 percent by weight of the derivative dimethicone of from about 15 mN/m to about 50 mN/m, such as from about 26 mN/m to about 37 mN/m.

In another embodiment of the present disclosure, instead of or in addition to containing a warming agent, the composition may contain a cleaning solvent. In this embodiment, for instance, the composition may include a cleaning solvent in conjunction with the derivatized dimethicone and one or more surface tension adjusting agents.

The cleaning solvent may comprise, for instance, an alcohol, an acetamide, d-limonene, methylsoyate, or any suitable hydrocarbon solvent. Other hydrocarbon solvents that may be present as the cleaning solvent include a dibasic ester, a terpene, a mineral spirit, a naphtha, other petroleum distillates, halogenated solvents, and the like. Still other particular cleaning solvents that may be present include acetone, ethyl acetate, methyl ethyl ketone, toluene, N,N-dimethylacetamide, methylene chloride, a monofunctional alcohol or mixtures thereof.

When containing a cleaning solvent, the surface tension adjusting agent may comprise an agent that either increases the surface tension or decreases the surface tension. The surface tension adjusting agent, for instance, may comprise a diol, an alcohol (that is different than the cleaning solvent), water, or the like. Various diols and water, for instance, can raise the surface tension of the resulting composition. Diols that may be used include various glycols such as butylene glycol, propylene glycol, polyethylene glycol, ethoxydiglycol, hexylene glycol, and the like.

The cleaning solvent can be present in the composition in any amount sufficient to carry out an intended purpose of the resulting product. For instance, the cleaning solvent can be present in the composition in an amount from about 20 percent by weight to about 90 percent by weight, such as from about 30 percent by weight to about 70 percent by weight. One or more surface tension adjusting agents are added into the composition in an amount sufficient to adjust the surface tension so that the composition will foam in the presence of the foaming agent. For instance, all of the cleaning solvents and all of the surface tension adjusting agents present in the composition can have a weighted average surface tension based on 10 percent by weight of the derivatized dimethicone of from about 15 mN/m to about 50 mN/m, such as from about 20 mN/m to about 45 mN/m, such as from about 26 mN/m to about 37 mN/m.

Other features and aspects of the present disclosure are discussed in greater detail below.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the following figures.

Figure 1:
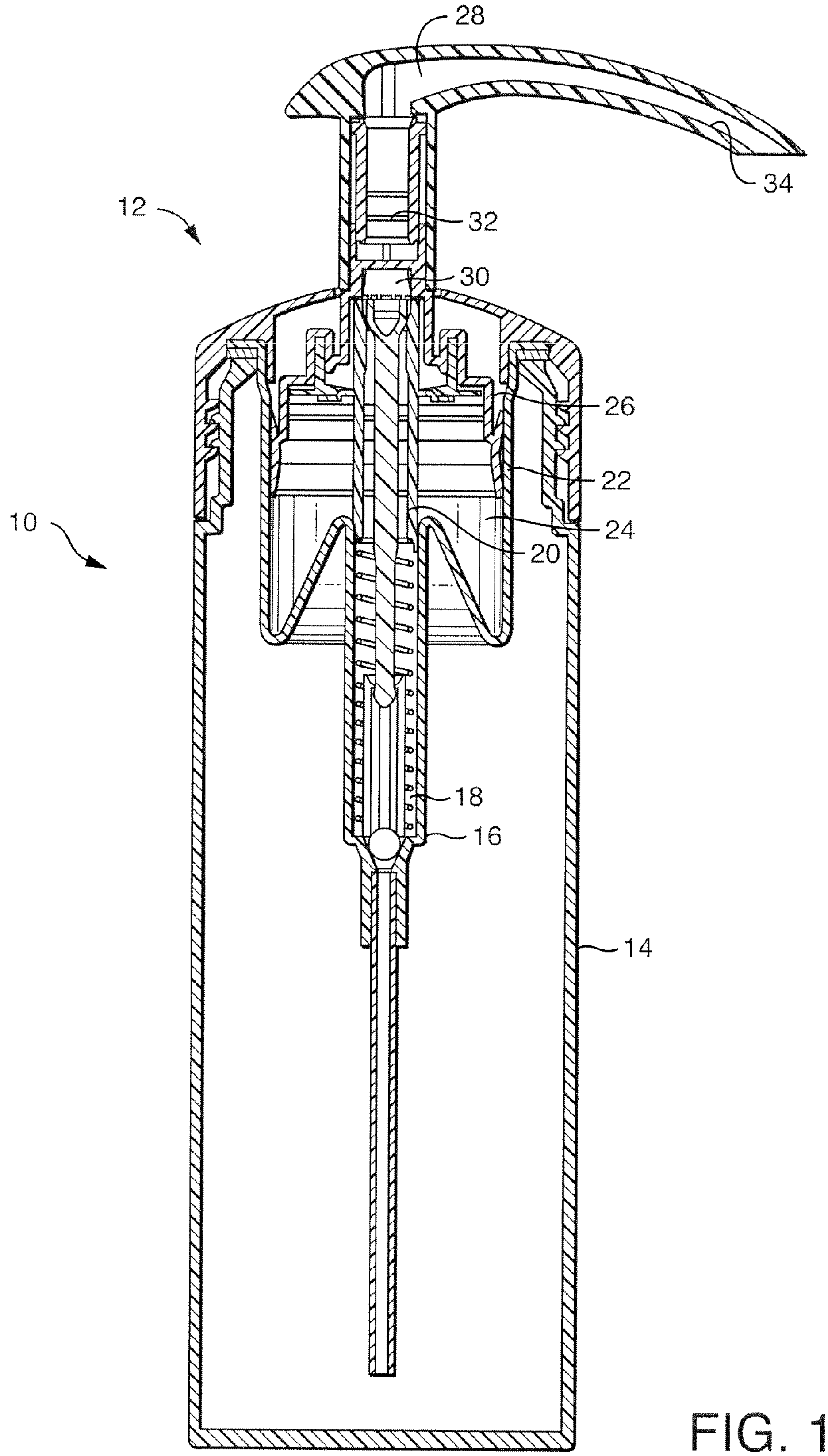
FIG. 1 is a cross-sectional view of one embodiment of a dispensing container that may be used in accordance with the present disclosure.

Repeat use of reference characters in the present specification and drawings is intended to represent same or analogous features or elements of the disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to various foamable compositions. The foamable compositions of the present disclosure contain at least one active ingredient. The active ingredient can comprise a useful chemical that has traditionally been difficult to incorporate into a composition that foams when combined with a gas. According to the present disclosure, the active ingredient can be combined with a particular foaming agent in conjunction with one or more surface tension adjusting agents. The surface tension adjusting agents adjust the surface tension of the resulting composition so that the foaming agent can affectively cause the composition to foam when combined with air and emitted from a container.

In the past, many foaming compositions contained water as the foam carrier. Water is a polar solvent that is generally easy to foam when combined with various surfactants. Water, however, can adversely interfere with many active ingredients when present in large quantities. For instance, some active ingredients may not foam when combined with water and/or water may adversely interfere with the properties of some active ingredients. Of particular advantage, the foamable compositions of the present disclosure can be formulated without using water as a carrier. In fact, in one embodiment, compositions can be formulated that contain less than 20 percent by weight water, such as less than 10 percent by weight water, such as less than 5% by weight water or may be completely anhydrous.

The active ingredients incorporated into the foamable compositions of the present disclosure can vary widely depending upon the particular application and the desired result. In one embodiment, for instance, the active ingredient incorporated in the foamable composition may comprise a cleaning solvent. For example, various different cleaning solvents can be incorporated into the composition in one embodiment, for instance, the cleaning solvent may comprise an industrial solvent used for removing grease and/or paint. Other cleaning solvents that may be incorporated into the composition include makeup and nail polish removers, hand degreasing agents, bathroom cleaners, and the like. Many of these solvents actually have defoaming properties. As will be described in greater detail below, however, the solvents can be still incorporated into compositions made in accordance with the present disclosure and remain foamable.

In addition to cleaning solvents, various other active ingredients can also be incorporated into the composition. For instance, in an alternative embodiment, the active ingredient may comprise a skin care agent that must be used in an anhydrous state. For instance, in one embodiment, an anhydrous warming agent may be incorporated into the composition. Warming agents can comprise various chemical species that generate heat when contacted with water. Warming agents, for instance, may be incorporated into various personal care products.

In addition to warming agents, various other hydrophobic and/or anhydrous agents may be incorporated into the composition of the present disclosure. Other such active ingredients include, for instance, hydrophobic vitamins and skin actives. In still another embodiment, the skin care agent may comprise a sunscreen agent that provides better protection to the skin when contained in an anhydrous system.

In order to incorporate the above described active ingredients into a composition capable of foaming, in accordance with the present disclosure, the active ingredients are combined with a foaming agent and one or more surface tension adjusting agents.

The foaming agent generally comprises one or more derivatized dimethicones. Derivatized dimethicones that may be used in the present disclosure include dimethicone copolyols and dimethicone copolyol esters, including ethoxylated dimethicones. Dimethicone copolyols generally include a dimethicone backbone with unprotected ethylene oxide pendant groups. The molecules can exist as multi-pendant or linear dimethicone copolyols. A linear dimethicone copolyol is as follows:

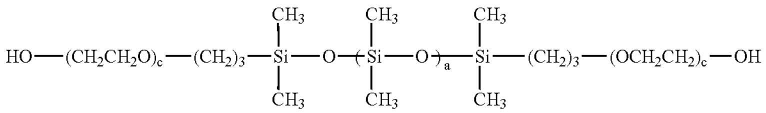

wherein A is from 1 to about 2000 and C is from 1 to about 30. A multi-pendant dimethicone copolyol is as follows:

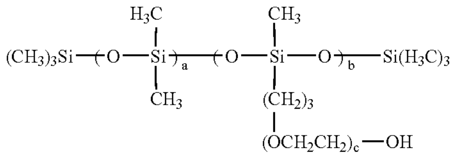

wherein A is from 1 to about 2000, B is from about 1 to about 20, and C is from about 1 to about 30.

Although multi-pendant dimethicone copolyols may be desirable in some applications, linear dimethicone copolyols have thus far shown better foaming properties. Although unknown, it is believed that the linear molecules include polar ethylene oxide branches that can more readily participate in hydrogen bonding between the active agent and other components contained within the composition. Thus, the linear molecules are capable of stabilizing individual bubbles within the foam. In addition, the linear nature of the molecules may form bridges between bubbles with one polar end inserted into the lamella of one bubble and the other polar end inserted into the lamella of an adjacent bubble within the foam. Further, the silicone-silicone interactions in linear molecules may also contribute to a cross-linked network within and in between films adding excellent stability to the foam and an increase in the quality and quantity of foam generated when the composition is aerated. Multi-pendant dimethicone copolyols are also well suited to stabilizing single bubbles as described above.

Dimethicone copolyols that may be used in the composition of the present disclosure include, in one embodiment, for instance, polyoxyethylene glycol dimethicones containing from about 2 moles of polyoxyethylene glycol to about 40 moles of polyoxyethylene glycol, such as containing from about 5 moles of polyoxyethylene glycol to about 20 moles of polyoxyethylene glycol. Particular examples of dimethicone copolyols that are well suited for use in the composition of the present disclosure include PEG-8 dimethicone, PEG-10 dimethicone, PEG-12 dimethicone, and mixtures thereof. In one particular embodiment, for instance, PEG-10 dimethicone may be mixed with PEG-12 dimethicone.

Dimethicone copolyol esters, on the other hand, generally include a dimethicone backbone with ethylene oxide pendant groups end-blocked with a fatty acid derivative. For instance, the structure of a dimethicone copolyol ester is as follows:

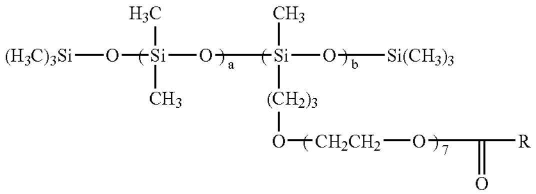

wherein R is derived from a fatty acid, A is from about 1 to about 2000 and B is from about 1 to about 30.

Fatty acids that may be used to form the dimethicone copolyol ester include fatty acids having a carbon chain from about 6 carbon atoms to about 30 carbon atoms. The fatty acid, for instance, may be derived from avocado, olive, coconut, soybean, and the like. Particular fatty acids that may be present in the dimethicone copolyol ester include decanoic acid, lauric acid, dodecanoic acid, palmitic acid, myristic acid, stearic acid, oleic acid, and mixtures thereof.

In the above formula, the dimethicone copolyol ester is shown containing 7 moles of polyoxyethylene glycol. It should be understood, however, that the dimethicone copolyol ester may contain more or less polyoxyethylene glycol. For instance, the ester may contain from about 2 moles to about 20 moles of PEG. The ethylene oxide pendant group is polar in nature and allows for hydrogen bonding with other polar molecules that may be within the composition. The fatty acid chain can participate in hydrophobic interactions with other components in the composition to add stability. The siloxane backbone, on the other hand, can participate in silicone-silicone interactions to further stabilize the foam.

The amount of derivatized dimethicone present within the composition can depend upon various factors including the active agent contained in the composition, the desired result, the manner in which the composition is to be dispensed, and the end use application for the composition. In general, for instance, the composition can contain the derivatized dimethicone in an amount from about 0.5 percent to about 30 percent by weight, such as from about 3 percent to about 25 percent by weight. In one embodiment, the composition contains the derivatized dimethicone in an amount of about 10 percent by weight.

In addition to one or more active agents and one or more derivatized dimethicones, the composition further contains one or more surface tension adjusting agents. The surface tension adjusting agents are added to the composition in order to either increase surface tension or decrease surface tension. More particularly, the surface tension adjusting agents are added to the composition so that the surface tension of the active agents in conjunction with the surface tension adjusting agents are within a specified range that permits foaming of the composition when the foaming agent is present. Based on a constant value of 10% derivatized dimethicone and 90% other ingredients, the present inventors have discovered that the compositions of the present disclosure are particularly foamable when the sum weighted surface tension of the ingredients before adding the derivatized dimethicone foaming agent falls within a range (at 25° C.) of from about 15 mN/m to about 50 mN/m, such as from about 20 mN/m to about 45 mN/m, such as from about 26 mN/m to about 37 mN/m.

If more or less than 10 percent derivatized dimethicone is present in the composition, then the weighted surface tension of the other ingredients can be converted to the above scale at the concentrations used in the formulation by using the following conversion equation:

$$0.90(w)=(p)(x)$$

wherein w is the calculated sum weighted surface tension for the active agents and the surface tension adjusting agents at their actual concentrations used in the composition; p is the total weighted percentage of the active agents and surface tension adjusting agents present in the composition expressed as a decimal; and x is the converted sum weighted surface tension. Thus, as used herein, the phrase "sum weighted surface tension based on 10 percent of weight of the derivatized dimethicone" is as calculated above or is the actual sum weighted surface tension if the composition contains 10 percent by weight of derivatized dimethicones.

To have the surface tension of the composition fall within the range as described above, one or more surface tension adjusting agents may be added to the composition. In general, any suitable surface tension adjusting agent may be used in the compositions of the present disclosure as long as the surface tension adjusting agents do not adversely interfere with the other components. Examples of surface tension adjusting agents that may be used in the present disclosure include diols, alcohols, water, or mixtures thereof.

Diols, for instance, generally serve to raise the surface tension of the composition. Diols that may be used as the surface tension adjusting agent may comprise, for instance, various glycols. Particular glycols that may be used include butylene glycol, propylene glycol, polyethylene glycol, ethoxydiglycol, hexylene glycol, 1,2-Hexanediol and mixtures thereof.

In certain embodiments, water may also be used in order to adjust the surface tension of the composition. Similar to diols, water also raises the surface tension. In some embodiments, however, water is substantially absent from the composition.

In order to lower the surface tension of the compositions, in one embodiment, the surface tension adjusting agent may comprise an alcohol. In general, any suitable alcohol may be used. For instance, in one embodiment, a monofunctional alcohol may be incorporated into the composition in order to lower surface tension. Particular examples of alcohols that may be used include ethanol, propanol, and the like.

The particular surface tension adjusting agents incorporated into the composition of the present disclosure and the amount of each agent depends upon the active agent present within the composition. For instance, the active agent may comprise a cleaning solvent. For instance, various different types of cleaning solvents may be formulated into foamable compositions in accordance with the present disclosure. In this particular embodiment, for instance, the cleaning solvent may comprise an industrial degreaser or paint remover. These types of solvents typically act as defoaming agents and thus are somewhat difficult to incorporate into foamable compositions in any great quantities. The above cleaning solvents, however, are typically applied with a rag or brush and thus often run or drip onto undesired areas. Having the capability to apply the above types of solvents as a foam may provide various advantages and benefits. A foaming composition, for instance, would maintain its placement onto a surface for a longer period of time and may be applied directly into tight spaces.

In addition to cleaning solvents adapted to remove grease and paint, other cleaning solvents that may be incorporated into compositions according to the present disclosure include cleaning solvents that can remove makeup and nail polish. Hand cleaning and degreasing solvents may also be incorporated into the composition. In still another embodiment, the cleaning solvent may comprise a solvent well suited to cleaning countertops, bathrooms, toilets, sinks, and the like.

A non-exhaustive list of cleaning solvents that may be incorporated into foamable compositions in accordance with the present disclosure include, for instance, alcohols, acetamides, d-limonene, methylsoyate, and various hydrocarbon cleaning solvents. Synthetic and natural hydrocarbon cleaning solvents that may be incorporated into the composition may include, for instance, dibasic esters, terpenes, mixtures of isoprenoid and mineral oil substances, naphthas, glycol ethers, parrafinic and isoparrafinic hydrocarbons, aromatic hydrocarbons, petroleum distillates, vegetable oils, animal oils, organic halides, halogenated solvents, mineral spirits, and the like. Other particular cleaning solvents that may be incorporated into the composition include acetone, ethyl acetate, methyl ethyl ketone, toluene, N,N-diethyl acetamide, methylene chloride, or mixtures thereof.

In one embodiment, the cleaning solvent may comprise an alcohol, such as a monofunctional alcohol. For instance, in one embodiment, the cleaning solvent may comprise ethanol. As described above, ethanol may also serve as a surface tension adjusting agent. When ethanol is present as a cleaning solvent, however, other different types of surface tension adjusting agents may be present.

The amount of cleaning solvent present in the composition can vary depending upon the particular application. In general, however, the cleaning solvent may be present in an amount from about 20 percent by weight to about 90 percent by weight. For instance, in one embodiment, one or more cleaning solvents may be present in the composition in an amount from about 30 percent by weight to about 70 percent by weight.

When a cleaning solvent is present, one or more surface tension adjusting agents may be present in the composition in an amount from 0 percent to about 70 percent by weight, such as from about 20 percent to about 60 percent by weight. More importantly, however, the surface tension adjusting agents are present in the composition sufficient so that the composition has a surface tension within a desired range.

In addition to cleaning solvents, in other embodiments, the active agent may comprise a skin care agent. Particular skin care agents well suited for use in compositions of the present disclosure include skin care compositions that are most effective when incorporated into anhydrous systems or systems containing substantially no water. Such skin care agents include warming agents, sunscreen agents, vitamins, and other skin actives.

Warming agents that may be incorporated in the compositions of the present disclosure include glycerin, glycerin derivatives, glycols, and mixtures thereof.

Glycerin derivatives include various ethoxylated compounds formed from glycerin. For example, in one embodiment, the glycerin derivative may comprise methyl gluceth containing from about 5 moles to about 50 moles of ethoxylate.

Glycol warming agents include, for instance, butylene glycol, propylene glycol, polyethylene glycol, ethoxydiglycols, hexylene glycol and mixtures thereof. As described above, glycols may also be used in compositions of the present disclosure as surface tension adjusting agents. When present as the active agent, such as a warming agent, however, the one or more glycols may be present in conjunction with other surface tension adjusting agents.

Some examples of sunscreen agents that may by incorporated into the compositions are: aminobenzoic acis (PABA), avobenzone, cinoxate, dioxybenzone, homosalate, menthyl anthranilate, octocrylene, octyl methoxycinnamate, octyl salicylate, benzophenone-3, ethylhexy dimethyl PABA, phenylbenzimidole sulfonic acid, benzophenone-4, and trolamine salicylate. The composition may also include but is not limited to all current monographed organic sunscreens both oil and water soluble.

When a skin care agent as described above is incorporated into a composition in accordance with the present disclosure, typically the surface tension of the composition needs to be lowered in conjunction with the addition of a foaming agent to produce a composition that is readily foamable. Thus, in many embodiments, when adding a skin care agent into a composition in accordance with the present disclosure, a surface tension adjusting agent is added that lowers the surface tension. Such agents may include various alcohols, such as monofunctional alcohols. For instance, in one embodiment, a skin care agent may be combined with ethanol in proportions sufficient to bring the surface tension of the composition within a desired range. This desired range may be from about 15%-90% by weight, preferably from about 20%-80% by weight, and most preferred from about 30%-70% by weight.

The composition of the present disclosure may contain various other ingredients to impart desired characteristics to the composition. Examples of additives that may be added to the composition include detackifiers, fragrances, antimicrobial agents, surfactants, humectants, thickeners, emollients, dyes, preservatives, and the like.

Thickeners that may be used in the composition include various modified celluloses. For instance, the thickener may comprise ethyl cellulose, hydroxypropyl cellulose, carboxymethyl cellulose, hydroxypropyl methyl cellulose, hydroxyethyl methyl cellulose, and combinations thereof. Additionally the thickner may also comprise a fumed silica composition.

The composition can also contain various emollients. Particular emollients that may be used include ethoxylated and propoxylated alcohols, such as ethoxylated or propoxylated cetyl alcohols and ethoxylated lanolin.

The composition can also contain various preservatives to increase the shelf life of the composition. Some suitable preservatives that can be used in the present disclosure include, but are not limited to, Kathon CG®, which is a mixture of methylchloroisothiazolinone and methylisothiazolinone, and Neolone 950®, which is methylisothiazolinone, both are available from Rohm & Haas; Mackstat H 66 (available from McIntyre Group, Chicago, Ill.); DMDM hydantoin (e.g., Glydant Plus, Lonza, Inc., Fair Lawn, N.J.); Ethylhexylglycerin (Sensiva SC 50 by Schulke & Mayr); Phenoxyethanol (Phenoxyethanol by Tri-K Industries); Caprylyl Glycol (Lexgard O by Inolex Chemical Company); Symdiol 68T (Blend of 1,2-Hexanediol, Caprylyl Glycol and Tropolone) and Symocide PT (Blend of Phenoxyethanol and Tropolone) both by Symrise; EDTA and salts thereof; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; imidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

The amount of the preservative utilized in the composition can generally vary depending on the relative amounts of the other components present within the formulation. For example, in some embodiments, the preservative is present in the formulation in an amount between about 0.0001% to about 5% by weight, in some embodiments between about 0.001 to about 1% by weight, and in some embodiments, between about 0.1% to about 0.15% by weight of the formulation.

Still other optional ingredients that may be included in the foaming composition include, but are not limited to, antimicrobial agents, antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives, including botanical chemicals and proteins (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); hydrotropes (helps dissolve some antimicrobial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); natural moisturizing factors, amino acids, and the like.

The compositions may be prepared in any conventional manner, e.g. by a simple admixture of the components. For instance, in one embodiment, all of the ingredients can be added and mixed together at the same time at room temperature.

The composition is foamable in that the composition is specifically formulated to form a foam when aerated. For example, in one embodiment, the composition may be contained in an aerosol container. In an aerosol container, the composition is maintained under pressure sufficient to cause foam formation when dispensed.

Of particular advantage, however, the composition of the present disclosure is foamable without the necessity of being placed in an aerosol container. For instance, in an alternative embodiment, the composition may be contained in a manual dispensing foam pump container. The non-aerosol container, for instance, may entrain air in the foamable composition as it is dispensed.

For instance, referring to FIG. 1, one embodiment of a dispensing container generally 10 that may be used with the composition is illustrated. The dispensing container 10 includes a dispensing assembly 12 that is screwed onto a liquid container 14. The dispensing assembly 12 includes a liquid pump 16 that comprises a liquid pump chamber 18 and a liquid pump piston 20. The dispensing container further includes an air pump 22 with an air pump chamber 24 and an air pump piston 26. The liquid piston 20 and the air piston 26 are coupled to an actuating head 28.

In order to dispense a foam from the dispensing container 10, the actuating head 28 is displaced by being pressed downwardly causing the pistons 20 and 26 to move downwards as well. As the pistons 20 and 26 are moved downwards, the volumes of the chambers 18 and 24 are reduced causing air and liquid to enter a mixing chamber 30. The liquid and air mixture then passes through a screen or mesh 32 and into a dispenser 34.

After foam is dispensed through the dispenser 34, the actuating head 28 is released and thus returns to its initial position.

The present disclosure may be better understood with respect to the following examples.

Example 1

For exemplary purposes, the following foamable compositions were formulated in accordance with the present disclosure. After each listed composition is a calculation of the weighted average surface tension of the solvents (see table below) and surface tension adjusting agents based on 10 percent by weight of the derivatized dimethicone.

Surface tension of common solvents

| 20-26 mN/m | 26-37 mN/m | 37+ mN/m |
|---|---|---|
| Ethanol (22.10)* | Methylene Chloride (28.10)^ | Polyethylene Glycol 200 (43.50)* |
| Ethyl Acetate (23.75)** | Toluene (28.40)* | Water (72.80)* |
| Methyl Ethyl Ketone (24.60)* | Xylenes (28.90-30.10)* | Propylene Glycol (40.1)+ |
| d-Limonene (25.00)*** | N,N-Dimethyl Acetamide (36.70)* | Glycerin (63.00)+++ |
| Acetone (25.20)* | | Butylene Glycol (37.8)++ |

*Surface tension values of some common test liquids for surface energy analysis. http://www.surface-tension.de/ Accessed Jan. 24, 2007
**http://macro.lsu.edu/howto/solvents/Surface%20Tension.htm Accessed Feb. 15, 2007
***d-Limonene MSDS, PDM. Inc. Updated January 2003
+http://www.kicgroup.com/pg995usp.htm Accessed Feb. 15, 2007
++1,3-Butylene Glycol MSDS, Kyowa Hakko Chemical Co. Ltd. 2006
+++Surface Tension http://www3.interscience.wiley.com:8100/legacy/college/cutnell/0471713988/ste/ste.pdf Accessed Feb. 15, 2007
^http://www.solvaychemicals.com/chemicals/Solkane_141b_Surface_Treatment_Agents, Accessed Feb. 15, 2007

Sample 1 - d-Limonene Foam

| Component | Trade Name | Company | Description | % Weight |
|---|---|---|---|---|
| d-Limonene | d-Limonene | | Solvent | 60 |
| PEG-4 | Lumulse PEG 200 | | Surface Tension Adjusting Agent | 20 |
| PEG-12 Dimethicone | Dow Corning 5329 Performance Modifier | | Foaming Agent | 20 |

d-Limonene 25.00 mN/m * (0.60) = 15.00 mN/m
PEG-4 43.50 mN/m * (0.20) = 8.70 mN/m
Sum weighted surface tension = 23.7 mN/m
Conversion: 0.90(23.7 mN/m) = 0.80(x)
X = 26.66 mN/m Sample 2 - Acetone Foam

| Component | Trade Name | Company | Description | % Weight |
|---|---|---|---|---|
| Acetone | Acetone | | Solvent | 70 |
| Water | Water | | Surface Tension Adjusting Agent | 20 |
| PEG-10 Dimethicone | Silsurf di-1010 | | Foaming Agent | 10 |

Acetone: 25.20 mN/m * (0.70) = 17.64 mN/m
Water: 72.80 mN/m * (0.20) = 14.56 mN/m
Sum weighted surface tension = 32.20 mN/m Sample 3 - Ethyl Acetate Foam

| Component | Trade Name | Company | Description | % Weight |
|---|---|---|---|---|
| Ethyl Acetate | Ethyl Acetate | | Solvent | 40 |
| PEG-4 | Lumulse PEG 200 | | Surface Tension Adjusting Agent | 50 |
| PEG-10 Dimethicone | Silsurf di-1010 | | Foaming Agent | 10 |

Ethyl Acetate: 23.75 mN/m * (0.40) = 9.50 mN/m
PEG-4: 43.50 mN/m * (0.50) = 21.75 mN/m
Sum weighted surface tension = 31.25 mN/m

| Sample 4 - Methyl Ethyl Ketone Foam | | | | |
|---|---|---|---|---|
| Component | Trade Name | Company | Description | % Weight |
| Methyl Ethyl Ketone | Methyl Ethyl Ketone | | Solvent | 35 |
| PEG-4 | Lumulse PEG 200 | | Surface Tension Adjusting Agent | 55 |
| PEG-10 Dimethicone | Silsurf di-1010 | | Foaming Agent | 10 |

Methyl Ethyl Ketone: 24.60 mN/m * (0.35) = 8.61 mN/m

PEG-4: 43.50 mN/m * (0.55) = 23.93 mN/m

Sum weighted surface tension = 32.54 mN/m

| Sample 5 - Toluene Foam | | | | |
|---|---|---|---|---|
| Component | Trade Name | Company | Description | % Weight |
| Toluene | Toluene | | Solvent | 90 |
| PEG-10 Dimethicone | Silsurf di-1010 | | Foaming Agent | 10 |

Toluene: 28.40 mN/m

| Sample 6 - N,N-Dimethyl Acetamide Foam | | | | |
|---|---|---|---|---|
| Component | Trade Name | Company | Description | % Weight |
| N,N-Dimethyl Acetamide | N,N-Dimethyl Acetamide | | Solvent | 90 |
| PEG-10 Dimethicone | Silsurf di-1010 | | Foaming Agent | 10 |

N,N-Dimethyl Acetamide: 36.70 mN/m

| Sample 7 - Butylene Glycol Foam | | | | |
|---|---|---|---|---|
| Component | Trade Name | Company | Description | % Weight |
| 1,3 Butylene Glycol | Butylene Glycol | | Solvent | 60 |
| Denatured Ethanol, 190 Proof | SDA 40B | | Surface Tension Adjusting Agent | 30 |
| PEG-10 Dimethicone | Silsurf di-1010 | | Foaming Agent | 10 |

Butylene Glycol: 37.80 mN/m * (0.60) = 22.68 mN/m

Ethanol: 22.10 mN/m * (0.30) = 6.63 mN/m

Sum weighted surface tension = 29.31 mN/m

| Sample 8 - Propylene Glycol Foam | | | | |
|---|---|---|---|---|
| Component | Trade Name | Company | Description | % Weight |
| Propylene Glycol | Propylene Glycol | | Solvent | 50 |
| Denatured Ethanol, 190 Proof | SDA 40B | | Surface Tension Adjusting Agent | 40 |
| PEG-10 Dimethicone | Silsurf di-1010 | | Foaming Agent | 10 |

Propylene Glycol: 40.10 mN/m * (0.50) = 20.05 mN/m

Ethanol: 22.10 mN/m * (0.40) = 8.84 mN/m

Sum weighted surface tension = 28.89 mN/m

| Sample 9 - Alcohol Foam | | | | |
|---|---|---|---|---|
| Component | Trade Name | Company | Description | % Weight |
| Denatured Ethanol, 190 Proof | SDA 40B | | Solvent | 62 |
| Water | Water | | Surface Tension Adjusting Agent | 28 |
| PEG-10 Dimethicone | Silsurf di-1010 | | Foaming Agent | 10 |

Ethanol: 22.10 mN/m * (0.62) = 13.70 mN/m

Water: 72.80 mN/m * (0.28) = 20.38 mN/m

Sum weighted surface tension = 34.08 mN/m

| Sample 10 - Foaming Nail Polish Remover | | | | |
|---|---|---|---|---|
| Component | Trade Name | Company | Description | % Weight |
| Acetone | Acetone | | Solvent | 20 |
| Ethyl Acetate | Ethyl Acetate | | Solvent | 20 |
| PEG-4 | Lumulse PEG 200 | | Surface Tension Adjusting Agent | 50 |
| PEG-10 Dimethicone | Silsurf di-1010 | | Foaming Agent | 10 |

Acetone: 25.20 mN/m * (0.20) = 5.04 mN/m

Ethyl Acetate: 23.75 mN/m * (0.20) = 4.75 mN/m

PEG-4: 43.50 mN/m * (0.50) = 21.75 mN/m

Sum weighted surface tension = 31.54 mN/m

| Sample 11 - Foaming Paint Stripper/Varnish Remover | | | | |
|---|---|---|---|---|
| Component | Trade Name | Company | Description | % Weight |
| Acetone | Acetone | | Solvent | 20 |
| Methylene Chloride | Methylene Chloride | | Solvent | 20 |
| PEG-4 | Lumulse PEG 200 | | Surface Tension Adjusting Agent | 50 |
| PEG-10 Dimethicone | Silsurf di-1010 | | Foaming Agent | 10 |

Acetone: 25.20 mN/m * (0.20) = 5.04 mN/m

Methylene Chloride; 28.10 mN/m * (0.20) = 5.62 mN/m

PEG-4: 43.50 mN/m * (0.50) = 21.75 mN/m

Sum weighted surface tension = 32.41 mN/m

Example 2

The following are exemplary foamable compositions containing an acetamide cleaning solvent. In this example the following compositions were formulated and then tested for foam quality. The compositions were used to illustrate that foaming has an optimal surface tension range and above and below that range, the foam is less than optimal. The foam quality is based upon observations of the foam once formed. The following scale was used to characterize the foam.

| Quality of Foam | Description |
|---|---|
| 1 | Tight cohesive foam, maintains integrity for 30 seconds |
| 2 | Foam begins cohesive, but degrades within 30 seconds |
| 3 | Loose foam; loses integrity nearly immediately |
| 4 | Wet, loose foam (bubbles); not cohesive |

| Sample 12 | | | | |
| --- | --- | --- | --- | --- |
| Component | Trade Name | Company | Description | % Weight |
| N,N-Dimethyl Acetamide | N,N-Dimethyl Acetamide | | Solvent | 35 |
| Denatured Ethanol, 190 Proof | SDA 40B 190 Proof Ethanol | | Surface Tension Adjusting Agent | 55 |
| PEG-10 Dimethicone | Silsurf di-1010 | | Foaming Agent | 10 |

N,N-Dimethyl Acetamide: 37.70 mN/m * (0.35) = 13.20 mN/m
Ethanol = 22.10 mN/m * (0.55) = 12.16 mN/m
Sum weighted surface tension = 25.36 mN/m
Foam Quality: 3

| Sample 13 | | | | |
| --- | --- | --- | --- | --- |
| Component | Trade Name | Company | Description | % Weight |
| N,N-Dimethyl Acetamide | N,N-Dimethyl Acetamide | | Solvent | 50 |
| PEG-4 | Lumulse PEG 200 | | Surface Tension Adjusting Agent | 40 |
| PEG-10 Dimethicone | Silsurf di-1010 | | Foaming Agent | 10 |

N,N-Dimethyl Acetamide: 37.70 mN/m * (0.50) = 18.85 mN/m
PEG-4: 43.50 mN/m * (0.40) = 17.40 mN/m
Sum weighted surface tension = 36.25 mN/m
Foam Quality: 1

| Sample 14 | | | | |
| --- | --- | --- | --- | --- |
| Component | Trade Name | Company | Description | % Weight |
| N,N-Dimethyl Acetamide | N,N-Dimethyl Acetamide | | Solvent | 20 |
| PEG-4 | Lumulse PEG 200 | | Surface Tension Adjusting Agent | 70 |
| PEG-10 Dimethicone | Silsurf di-1010 | | Foaming Agent | 10 |

N,N-Dimethyl Acetamide: 37.70 mN/m * (0.20) = 7.54 mN/m
PEG-4: 43.50 mN/m * (0.70) = 30.45 mN/m
Sum weighted surface tension = 37.99 mN/m
Foam Quality: 2

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed is:

1. A foamable composition comprising:

a foaming agent comprising a derivatized dimethicone, the derivatized dimethicone including at least one polar end;

a surface tension adjusting agent that is present in the composition in an amount sufficient to lower surface tension;

a warming agent comprising glycerin, a glycerin derivative, a glycol, or mixtures thereof;

wherein the surface tension adjusting agent and the warming agent are present in the composition such that they have a weight average surface tension from about 15 mN/m to about 50 mN/m; and wherein the composition contains substantially no water.

2. A foamable composition as defined in claim 1, wherein the composition is anhydrous.

3. A foamable composition as defined in claim 1, wherein the surface tension adjusting agent comprises a monofunctional alcohol.

4. A foamable composition as defined in claim 1, wherein the surface tension adjusting agent comprises ethanol.

5. A foamable composition as defined in claim 1, wherein the warming agent comprises glycerin.

6. A foamable composition as defined in claim 1, wherein the warming agent comprises a glycerin derivative, the glycerin derivative comprising an ethoxylated glycerin.

7. A foamable composition as defined in claim 6, wherein the glycerin derivative comprises a methyl gluceth having from about 5 moles to about 50 moles of ethoxylate.

8. A foamable composition as defined in claim 1, wherein the warming agent comprises a glycol, the glycol comprising a butylene glycol, a propylene glycol, a polyethylene glycol, an ethoxydiglycol, a hexylene glycol, or mixtures thereof.

9. A foamable composition as defined in claim 1, wherein the derivatized dimethicone comprises a dimethicone copolyol.

10. A foamable composition as defined in claim 1, wherein the derivatized dimethicone contains a linear polyoxyethylene glycol dimethicone having from about 5 moles to about 20 moles of polyoxyethylene glycol.

11. A foamable composition as defined in claim 1, wherein the derivatized dimethicone comprises polyoxyethylene glycol dimethicone containing about 10 moles of polyoxyethylene glycol, polyoxyethylene glycol dimethicone containing about 12 moles of polyoxyethylene glycol or mixtures thereof, the polyoxyethylene glycol dimethicones being linear and being present in the composition in an amount from about 3 percent to about 15 percent by weight.

12. A dispensing container containing the foamable composition as defined in claim 1, the dispensing container including a manual pump that converts the foamable composition into a foam when manually operated.

13. A foamable composition as defined in claim 1, wherein the derivatized dimethicone is present in the composition in an amount from about 3 percent to about 30 percent by weight.

14. A foamable composition as defined in claim 1, wherein the warming agent is present in the composition in an amount from about 15 percent to about 90 percent by weight and wherein the surface tension adjusting agent is present in the composition in an amount from about 0.1 percent to about 30 percent by weight.

15. A foamable composition as defined in claim 1, wherein the surface tension adjusting agent and the warming agent are present in the composition such that they have a weight average surface tension based on 10 percent by weight derivatized dimethicone of from about 26 mN/m to about 37 mN/m.

16. A foamable composition comprising:

at least one cleaning solvent comprising an alcohol, an acetamide, a ketone, an ester, a halogenated hydrocarbon, an aromatic hydrocarbon, or mixtures thereof;

a foaming agent comprising a derivatized dimethicone, the derivatized dimethicone including at least one polar end;

a surface tension adjusting agent comprising a diol, a monofunctional alcohol, or mixtures thereof; and wherein the composition contains substantially no water and all cleaning solvents and all surface tension adjusting agents present in the composition have a weight average surface tension based on the composition containing 10 percent by weight of the derivatized dimethicone of from about 15 mN/m to about 50 mN/m.

17. A foamable composition as defined in claim 16, wherein the solvent comprises d-limonene, methyl soyate, acetone, ethyl acetate, methyl ethyl ketone, toluene, N,N-dimethylacetamide, a monofunctional alcohol, methylene chloride, methyl isobutyl ketone, N,N-dimethylformamide or mixtures thereof.

18. A foamable composition as defined in claim 16, wherein the surface tension adjusting agent comprises the diol, the diol comprising a glycol, the glycol comprising a butylene glycol, a propylene glycol, a polyethylene glycol, an ethoxydiglycol, a hexylene glycol, or mixtures thereof.

19. A foamable composition as defined in claim 16, wherein the surface tension adjusting agent comprises the alcohol and is different than the cleaning solvent.

20. A foamable composition as defined in claim 19, wherein the cleaning solvent is present in the composition in an amount from about 30 percent to about 70 percent by weight, and the surface tension adjusting agent is present in the composition in an amount from about 20 percent to about 60 percent by weight.

21. A foamable composition as defined in claim 16, wherein all the cleaning solvents and all the surface tension adjusting agents present in the composition have a weighted average surface tension based on the composition containing 10 percent by weight of the derivatized dimethicone of from about 20 mN/m to about 45 mN/m.

22. A foamable composition as defined in claim 16, wherein the derivatized dimethicone is present in the composition in an amount from about 3 percent to about 30 percent by weight.

23. A foamable composition as defined in claim 16, wherein the derivatized dimethicone comprises a linear polyoxyethylene glycol dimethicone having from about 5 moles to about 20 moles of polyoxyethylene glycol.

24. A foamable composition comprising:

a cleaning solvent comprising acetone;

a foaming agent comprising a derivatized dimethicone, the derivatized dimethicone including at least one polar end;

at least one surface tension adjusting agent comprising water; and wherein all cleaning solvents and all surface tension adjusting agents present in the composition have a weight average surface tension based on the composition containing 10% by weight of the derivatized dimethicone of from about 15 mN/m to about 50 mN/m.

25. A foamable composition as defined in claim 24, wherein the derivatized dimethicone is present in the composition in an amount from about 3 percent to about 30 percent by weight.

26. A foamable composition as defined in claim 24, wherein the derivatized dimethicone comprises a linear polyoxyethylene glycol dimethicone having from about 5 moles to about 20 moles of polyoxyethylene glycol.

27. A foamable composition as defined in claim 24, wherein the cleaning solvent is present in the composition in an amount from about 20% to about 90% by weight and the surface tension adjusting agent is present in the composition in an amount from about 5% to about 60% by weight.

* * * * *